US012221429B2

(12) United States Patent
Liu et al.

(10) Patent No.: US 12,221,429 B2
(45) Date of Patent: Feb. 11, 2025

(54) METHOD FOR SYNTHESIZING 1,3,2-DIOXATHIOLANE 2,2-DIOXIDE BY IN-SITU CATALYTIC OXIDATION

(71) Applicant: Shandong Normal University, Shandong (CN)

(72) Inventors: Qikui Liu, Shandong (CN); Xiaomeng Zhang, Shandong (CN)

(73) Assignee: Shandong Normal University, Jinan (CN)

( * ) Notice: Subject to any disclaimer, the term of this patent is extended or adjusted under 35 U.S.C. 154(b) by 0 days.

(21) Appl. No.: 18/770,589

(22) Filed: Jul. 11, 2024

(65) Prior Publication Data

US 2024/0368111 A1    Nov. 7, 2024

Related U.S. Application Data

(63) Continuation of application No. PCT/CN2023/070353, filed on Jan. 4, 2023.

(30) Foreign Application Priority Data

Nov. 1, 2022   (CN) .......................... 202211353140.8

(51) Int. Cl.
| | | |
|---|---|---|
| C07D 327/10 | (2006.01) |
| B01J 23/52 | (2006.01) |
| B01J 29/89 | (2006.01) |
| B01J 37/00 | (2006.01) |
| B01J 37/04 | (2006.01) |
| B01J 37/18 | (2006.01) |

(52) U.S. Cl.
CPC ............ *C07D 327/10* (2013.01); *B01J 23/52* (2013.01); *B01J 29/89* (2013.01); *B01J 37/0045* (2013.01); *B01J 37/04* (2013.01); *B01J 37/18* (2013.01)

(58) Field of Classification Search
CPC ......... C07D 327/10; B01J 23/52; B01J 29/89; B01J 37/0045; B01J 37/04; B01J 37/18
USPC ........................................................ 549/34
See application file for complete search history.

(56) References Cited

FOREIGN PATENT DOCUMENTS

| | | |
|---|---|---|
| CN | 108707095 A | 10/2018 |
| CN | 109422719 A | 3/2019 |
| CN | 109988145 A | 7/2019 |
| CN | 110386916 A | 10/2019 |
| CN | 111909129 A | 11/2020 |
| CN | 112387305 A | 2/2021 |
| CN | 114917848 A | 8/2022 |
| WO | 2022092429 A1 | 5/2022 |

*Primary Examiner* — Taylor V Oh

(57) ABSTRACT

Disclosed is a method for synthesizing 1,3,2-dioxathiolane 2,2-dioxide (DTD) by in-situ catalytic oxidation. A titanium silicon (TS)-1 molecular sieve is modified with a Pd salt and an Au salt to obtain an Au—Pd/TS-1 molecular sieve, which catalyzes oxygen and hydrogen to form hydrogen peroxide, and oxidizes glycol sulfite in situ in a reactor to synthesize DTD. An Au—Pd/TS-1 molecular sieve catalyst prepared by the present disclosure, which has two catalytic activities of catalytic synthesis of hydrogen peroxide and catalytic oxidation of sulfite, can significantly increase the reaction rate, enable the complete conversion of raw materials in a shorter residence time, and effectively inhibit the hydrolysis of products, and a high-purity DTD product can be obtained by washing and evaporatively crystallizing an organic phase.

7 Claims, 4 Drawing Sheets

METHOD FOR SYNTHESIZING 1,3,2-DIOXATHIOLANE 2,2-DIOXIDE BY IN-SITU CATALYTIC OXIDATION

CROSS-REFERENCE TO RELATED APPLICATIONS

This application is a continuation of PCT/CN2023/070353, filed Jan. 4, 2023 and claims priority of Chinese Patent Application No. 202211353140.8, filed on Nov. 1, 2022, the entire contents of which are incorporated herein by reference.

TECHNICAL FIELD

The present disclosure relates to technical fields of organic synthesis and lithium ion batteries, and specifically to a method for synthesizing 1,3,2-dioxathiolane 2,2-dioxide (DTD) by in-situ catalytic oxidation.

BACKGROUND

Titanium silicon (TS)-1 molecular sieve is a zeolite molecular sieve material developed in 1980's. The TS molecular sieve with excellent directional oxidation performance was firstly formed by Enichem (Italy) by introducing titanium element into a molecular sieve skeleton with a zeolite socony mobil (ZSM)-5 structure. TS-1 catalyst, which shows excellent catalytic performance in low-temperature oxidation reaction with $H_2O_2$ as oxidant, such as mild reaction conditions, high catalytic activity and selectivity, and simple process flow, can overcome the shortcomings of long routes, many by-products and harsh reaction conditions in the conventional process, and plays a positive role in promoting the greening of chemical processes.

DTD, as a very important additive in lithium-ion batteries, can be oxidized to form a film on the positive electrode surface of lithium-ion batteries and reduced to a low impedance film on the negative electrode surface, to effectively improve the high and low temperature cycling performance of lithium-ion batteries and high temperature storage performance. In the existing methods of preparing alkyl sulfate by oxidizing alkyl sulfite, oxides, chlorides and complexes of the transition metal ruthenium are typically used as catalysts, and potassium permanganate, sodium hypochlorite and sodium periodate as oxidants. The ruthenium catalysts used are expensive, which bind to the substrate in the reaction system by means of complexation coordination, so it is difficult to recycle the catalysts at the end of the reaction, resulting in high production costs. In addition, oxidants such as potassium permanganate are used in the reaction, which produce a large amount of saline organic wastewater at the end of the reaction, increasing the cost of waste treatment and making the route uneconomical and non-environmentally friendly.

A patent with the number of CN109422719A reported that hydrogen peroxide was added dropwise to a mixture of cyclic sulfite, organic solvent and TS-1 molecular sieve catalyst for the catalytic oxidation reaction to prepare sulfate, but the problems are that: (1) the commercially available hydrogen peroxide is at a concentration of 28-30%, and the use of hydrogen peroxide of lower concentration will lead to a larger amount of water in the system, which is prone to the hydrolysis of glycol sulfite or DTD, resulting in a reduced yield (the yield of this patent is <60%); and (2) stabilizers need to be added during transportation and storage to inhibit the decomposition of hydrogen peroxide, and these stabilizers will reduce the effect of the use of hydrogen peroxide to a certain extent, and even affect the purity of products or increase the cost of removing these stabilizers.

SUMMARY

To solve the problems of low concentration, weak oxidative activity, long reaction time, large hydrolysis loss of raw materials or products, and low product yield of the conventional hydrogen peroxide, an objective of the present disclosure is to provide a method for synthesizing DTD by in-situ catalytic oxidation, in which, hydrogen peroxide is generated in situ and is used for synthesizing DTD by catalytic oxidation.

To realize the above objective, the present disclosure employs the following technical solutions.

A method for synthesizing DTD by in-situ catalytic oxidation includes the following steps:

(1) preparation of Au—Pd/TS-1 catalyst: dissolving a Pd salt and an Au salt in water, adding a TS-1 molecular sieve, followed by stirring uniformly, reacting for 8-24 h at a temperature raised to be 60-105° C., to obtain a reaction liquid, performing air-blast drying on the reaction liquid to remove water to obtain white powder, and putting the obtained white powder into a tube furnace for reduction treatment at 350-450° C. for 2-3 h to obtain an Au—Pd/TS-1 catalyst, the tube furnace having an atmosphere of a gas mixture of hydrogen and argon, and the hydrogen in the gas mixture being at a volume concentration of 5-10%;

the Pd salt being one or two of $PdCl_2$, $PdSO_4$, $Pd(NO_3)_2 \cdot 2H_2O$ or $Pd(OAc)_2$;

the Au salt being $AuCl_3$ and/or $HAuCl_4 \cdot 3H_2O$; and a mass ratio of the Pd salt, the Au salt, the TS-1 molecular sieve and water being 8-12 g:8-15 g:0.9-1 kg:1-5 kg;

(2) preparation of raw materials: mixing the Au—Pd/TS-1 catalyst obtained in step (1) with water to obtain a suspension liquid at a mass concentration of 1-10%; and mixing glycol sulfite with dichloroethane to prepare a glycol sulfite-dichloroethane solution with a mass fraction of glycol sulfite of 10-60%, for later use; and (3) continuous flow synthesis reaction: pumping the suspension liquid obtained in step (2) into a premixing zone of a flow reactor, introducing hydrogen and oxygen thereinto, and controlling a temperature of the premixing zone to be 10-90° C. and a residence time of the suspension liquid in the premixing zone to be 3-60 s, to obtain a premixed liquid, a volume ratio of the hydrogen to the oxygen being 1:1;

the premixed liquid entering a reaction zone after flowing out of the premixing zone, pumping the glycol sulfite-dichloroethane solution obtained in step (2) into the reaction zone at the same time, controlling a temperature of the reaction zone to be 10-90° C. and a residence time of a reaction to be 15-600 s, to obtain a reaction liquid, which flows out of the reactor, separating the Au—Pd/TS-1 catalyst by a filter, and processing an obtained filtrate by a centrifugal separator to obtain an aqueous phase and an organic phase; and adding the same volume of deionized water to the organic phase, followed by pumping into a centrifugal extractor for liquid separation to obtain an organic phase solution, and distilling and crystallizing the obtained organic phase solution to obtain a DTD product.

Preferably, the Pd salt is $PdCl_2$ or $Pd(OAc)_2$; and the Au salt is $HAuCl_4 \cdot 3H_2O$.

Preferably, a mass of water added in step (1) is twice a total mass of the TS-1 molecular sieve and the two metal salts.

Preferably, in step (3), a mass ratio of the suspension liquid obtained in step (2) to the gas mixture is 1:1-2.

Preferably, in step (3), a mass ratio of the glycol sulfite to the oxygen introduced into the premixing zone is 108:32-64.

Preferably, a temperature of the premixing zone is 60-65° C., and a temperature of the reaction zone is 50-55° C.

Preferably, the residence time of the suspension liquid in the premixing zone is 40-50 s, and the residence time of the reaction is 400-450 s.

Figure 1:
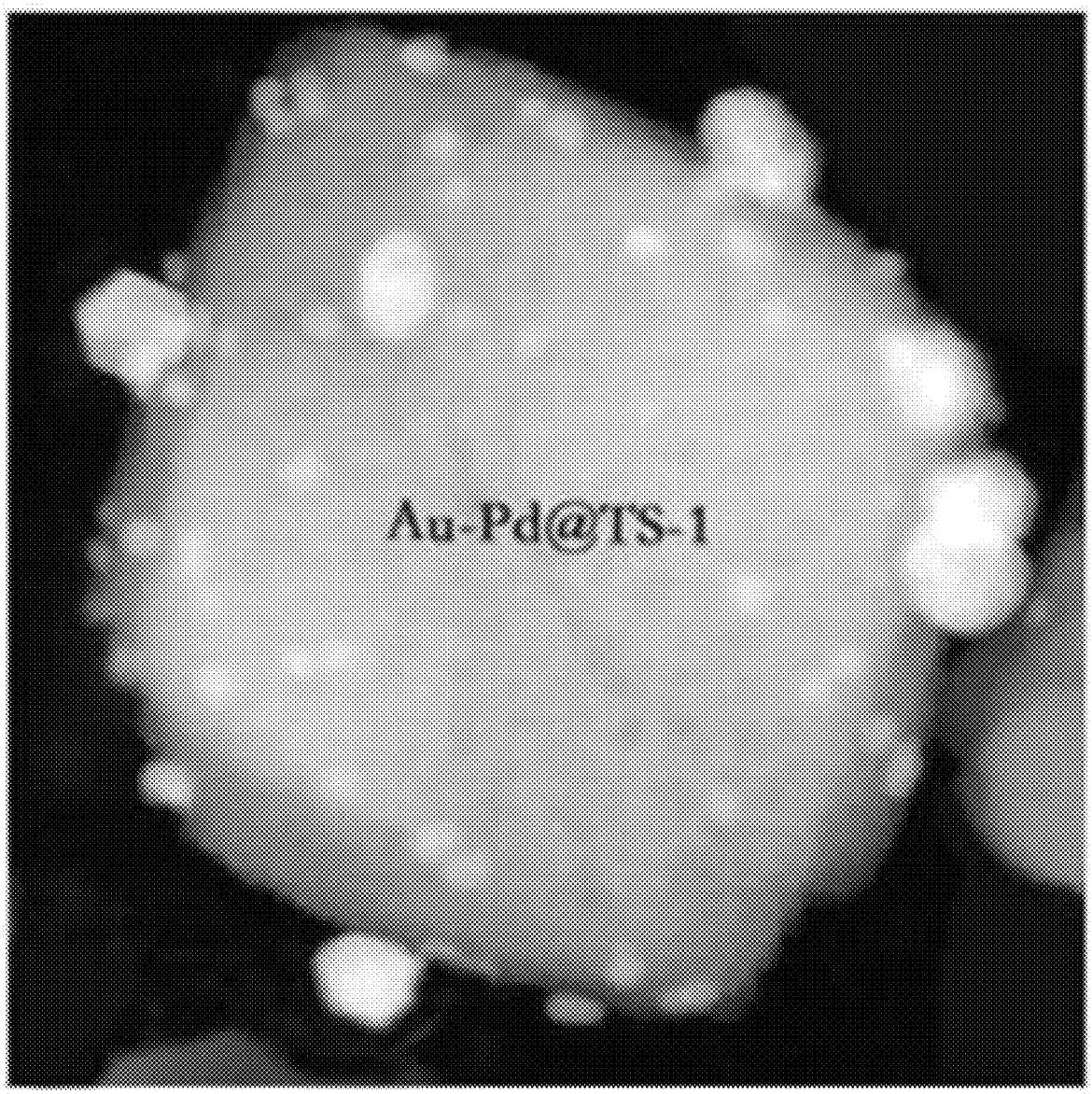
FIG. 1 shows the scanning electron microscope (SEM) characterization of an Au—Pd/TS-1 (Au—Pd@TS-1) catalyst.

The present disclosure has the following advantages over the prior art.

The Au—Pd/TS-1 catalyst prepared by the present disclosure realizes the efficient catalysis of two reactions at the same time. Firstly, the direct production of $H_2O_2$ from $H_2$ and $O_2$ gas streams as raw materials, with a conversion rate of >99%, and at the same time, the catalyst can synthesize sulfate by catalytic oxidation, which enables the present disclosure to realize the in-situ synthesis and consumption of $H_2O_2$, and further increases the conversion rate (>99 9%) of $H_2O_2$ synthesized from $H_2$ and $O_2$.

The activity of hydrogen peroxide has been significantly improved due to the realization of in-situ synthesis and use of hydrogen peroxide, combined with the efficient catalytic effect of the modified catalyst prepared by the present disclosure for the oxidation reaction of sulfite, the oxidation reaction rate of the present disclosure is greatly improved, so that the reaction can be completed in a very short period of time, which avoids the hydrolysis loss of raw materials and products caused by the prolonged contact with water, thus obtaining a very high yield.

The modified catalyst prepared by the present disclosure, which is based on the conventional TS-1 molecular sieve catalyst, has the structural characteristics of molecular sieve catalysts, features high stability, long service life, and low cost compared with the conventional ruthenium-based catalysts or other structural catalysts, and is especially suitable for the catalytic oxidation process of the weakly acidic system described in the present disclosure.

DETAILED DESCRIPTION

An objective of the present disclosure is to provide a method for synthesizing DTD by in-situ catalytic oxidation, and the present disclosure is further described below with specific examples.

A method for synthesizing DTD by in-situ catalytic oxidation includes the following steps.

(1) Preparation of Au—Pd/TS-1 catalyst: a Pd salt and an Au salt are dissolved in water, and a TS-1 molecular sieve is added, followed by stirring uniformly, and reacting for 8-24 h at a temperature raised to be 60-105° C., and a reaction liquid is obtained, which is subjected to air-blast drying to remove water to obtain white powder, which is put into a tube furnace for reduction treatment at 350-450° C. for 2-3 h to obtain an Au—Pd/TS-1 catalyst. The tube furnace has an atmosphere of a gas mixture of hydrogen and argon, and the hydrogen in the gas mixture is at a volume concentration of 5-10%.

The Pd salt is one or two of $PdCl_2$, $PdSO_4$, $Pd(NO_3)_2 \cdot 2H_2O$ or $Pd(OAc)_2$.

The Au salt is $AuCl_3$ and/or $HAuCl_4 \cdot 3H_2O$.

A mass ratio of the Pd salt, the Au salt, the TS-1 molecular sieve and water is 8-12 g:8-15 g:0.9-1 kg:1-5 kg.

(2) Preparation of raw materials: the Au—Pd/TS-1 catalyst obtained in step (1) is mixed with water to obtain a suspension liquid at a mass concentration of 1-10%; and glycol sulfite is mixed with dichloroethane to prepare a glycol sulfite-dichloroethane solution with a mass fraction of glycol sulfite of 10-60%, for later use.

Figure 3:
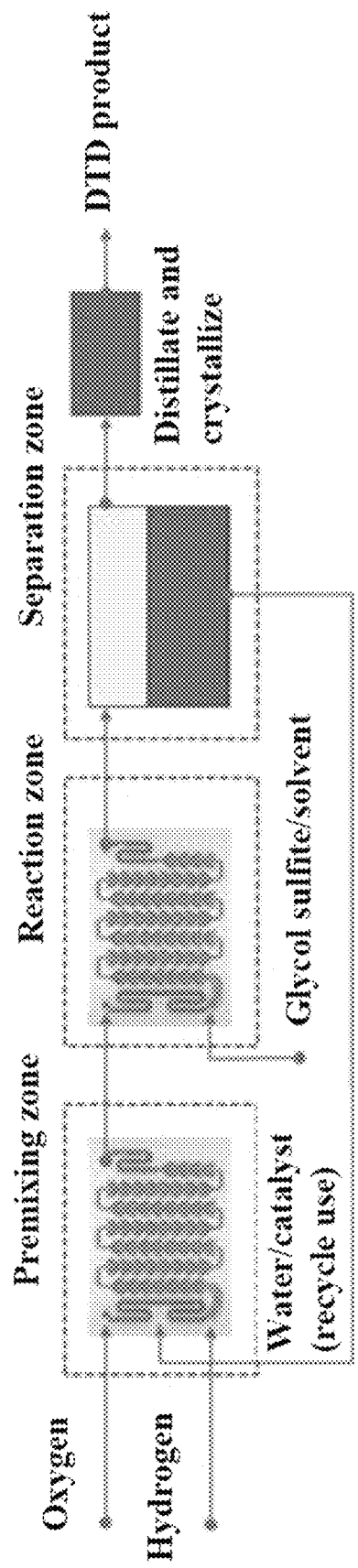
FIG. 3 shows a schematic diagram of the process flow of a method for synthesizing DTD by in-situ catalytic oxidation.

(3) Continuous flow synthesis reaction: as shown in FIG. 3, the suspension liquid obtained in step (2) is pumped into a premixing zone of a flow reactor, and hydrogen and oxygen are introduced thereinto; a temperature of the premixing zone is controlled to be 10-90° C., a residence time of the suspension liquid in the premixing zone is controlled to be 3-60 s, and a premixed liquid is obtained; and a volume ratio of the hydrogen to the oxygen is 1:1;

the premixed liquid enters a reaction zone after flowing out of the premixing zone, and the glycol sulfite-dichloroethane solution obtained in step (2) is pumped into the reaction zone at the same time; a temperature of the reaction zone is controlled to be 10-90° C., a residence time of a reaction is controlled to be 15-600 s, and a reaction liquid is obtained, which flows out of the reactor and enters a separation zone; and the Au—Pd/TS-1 catalyst is separated by a filter, and an obtained filtrate is processed by a centrifugal separator to obtain an aqueous phase and an organic phase; and the same volume of deionized water is added to the organic phase, followed by pumping into a centrifugal extractor for liquid separation to obtain an organic phase solution, and the obtained organic phase solution is distilled and crystallized to obtain a DTD product.

Preferably, the Pd salt is $PdCl_2$ or $Pd(OAc)_2$; and the Au salt is $HAuCl_4 \cdot 3H_2O$.

Preferably, a mass of water added in step (1) is twice a total mass of the TS-1 molecular sieve and the two metal salts.

Preferably, in step (3), a mass ratio of the suspension liquid obtained in step (2) to the gas mixture is 1:1-2.

Preferably, in step (3), a mass ratio of the glycol sulfite to the oxygen introduced into the premixing zone is 108:32-64.

Preferably, a temperature of the premixing zone is 60-65° C., and a temperature of the reaction zone is 50-55° C.

Preferably, the residence time of the suspension liquid in the premixing zone is 40-50 s, and the residence time of the reaction is 400-450 s.

Example 1 A method for synthesizing DTD by in-situ catalytic oxidation includes the following steps.

(1) Preparation of Au—Pd/TS-1 catalyst: 8 g of $PdCl_2$ and 8 g of $AuCl_3$ were dissolved in 1 kg of water, and 1 kg of TS-1 molecular sieve was added, followed by stirring uniformly, and reacting for 8 h at a temperature raised to be 60° C., and a reaction liquid was obtained, which was subjected to air-blast drying to remove water to obtain white powder, which was put into a tube furnace for reduction treatment at 350° C. for 2 h to obtain an Au—Pd/TS-1 catalyst. The tube furnace had an atmosphere of a gas mixture of hydrogen and argon, and a volume concentration of the hydrogen in the gas mixture was 5%.

(2) Preparation of raw materials: 100 g of the Au—Pd/TS-1 catalyst obtained in step (1) was taken and mixed with 9900 kg of water to obtain a suspension liquid; and 100 g of glycol sulfite was mixed with 900 g of dichloroethane to prepare a glycol sulfite-dichloroethane solution with a mass fraction of glycol sulfite of 10%, for later use.

(3) Continuous flow synthesis reaction: the suspension liquid obtained in step (2) was pumped into a premixing zone of a flow reactor, and at the same time, hydrogen and oxygen were introduced thereinto; a mass ratio of the suspension liquid to a sum of weights of the hydrogen and the oxygen was 1:1; a temperature of the premixing zone was controlled to be 10° C., a residence time of the suspension liquid in the premixing zone was controlled to be 60 s, and a premixed liquid was obtained; and a volume ratio of the hydrogen and the oxygen in the gas mixture was 1:1;

the premixed liquid entered a reaction zone after flowing out of the premixing zone, and at the same time, the glycol sulfite-dichloroethane solution obtained in step (2) was pumped into the reaction zone; a temperature of the reaction zone was controlled to be 10° C., a residence time of a reaction was controlled to be 600 s, and a reaction liquid was obtained, which flowed out of the reactor; the Au—Pd/TS-1 catalyst was separated by a filter, and an obtained filtrate was processed by a centrifugal separator to obtain an aqueous phase and an organic phase; a mass ratio of the glycol sulfite to the oxygen introduced into the premixing zone was 108:32; and a mass of the oxygen introduced into the premixing zone was 29.7 g; and the same volume of deionized water was added to the organic phase, followed by pumping into a centrifugal extractor for liquid separation to obtain an organic phase solution, and the obtained organic phase solution was distilled and crystallized to obtain a DTD product.

Example 2 A method for synthesizing DTD by in-situ catalytic oxidation includes the following steps.

(1) Preparation of Au—Pd/TS-1 catalyst: 12 g of $PdSO_4$ and 15 g of $HAuCl_4 \cdot 3H_2O$ were dissolved in 5 kg of water, and 900 g of TS-1 molecular sieve was added, followed by stirring uniformly, and reacting for 4 h at a temperature raised to be 105° C., and a reaction liquid was obtained, which was subjected to air-blast drying to remove water to obtain white powder, which was put into a tube furnace for reduction treatment at 450° C. for 3 h to obtain an Au—Pd/TS-1 catalyst. The tube furnace had an atmosphere of a gas mixture of hydrogen and argon, and the hydrogen in the gas mixture was at a volume concentration of 10%.

(2) Preparation of raw materials: 100 g of the Au—Pd/TS-1 catalyst obtained in step (1) was mixed with 900 g of water to obtain a suspension liquid at a mass concentration of 10%; and 600 g of glycol sulfite was mixed with 400 g of dichloroethane to prepare a glycol sulfite-dichloroethane solution with a mass fraction of glycol sulfite of 60%, for later use.

(3) Continuous flow synthesis reaction: the suspension liquid obtained in step (2) was pumped into a premixing zone of a flow reactor, and hydrogen and oxygen were introduced thereinto; a temperature of the premixing zone was controlled to be 90° C., a residence time of the suspension liquid in the premixing zone was controlled to be 3 s, and a premixed liquid is obtained; and a volume ratio of the hydrogen to the oxygen was 1:1;

the premixed liquid entered a reaction zone after flowing out of the premixing zone, and at the same time, the glycol sulfite-dichloroethane solution obtained in step (2) was pumped into the reaction zone; a temperature of the reaction zone was controlled to be 90° C., a residence time of a reaction was controlled to be 15 s, and a reaction liquid was obtained, which flowed out of the reactor; the Au—Pd/TS-1 catalyst was separated by a filter, and an obtained filtrate was processed by a centrifugal separator to obtain an aqueous phase and an organic phase; a mass ratio of the glycol sulfite to the oxygen introduced into the premixing zone was 108:64; and a mass of the oxygen introduced into the premixing zone was 355.5 g; and the same volume of deionized water was added to the organic phase, followed by pumping into a centrifugal extractor for liquid separation to obtain an organic phase solution, and the obtained organic phase solution was distilled and crystallized to obtain a DTD product.

Example 3 A method for synthesizing DTD by in-situ catalytic oxidation includes the following steps.

(1) Preparation of Au—Pd/TS-1 catalyst: 9 g of $Pd(NO_3)_2 \cdot 2H_2O$ and 10 g of $AuCl_3$ were dissolved in 2 kg of water, and 1 kg of TS-1 molecular sieve was added, followed by stirring uniformly, and reacting for 10 h at a temperature raised to be 80° C., and a reaction liquid was obtained, which was subjected to air-blast drying to remove water to obtain white powder, which was put into a tube furnace for reduction treatment at 400° C. for 2.5 h to obtain an Au—Pd/TS-1 catalyst. The tube furnace had an atmosphere of a gas mixture of hydrogen and argon, and the hydrogen in the gas mixture was at a volume concentration of 6%.

(2) Preparation of raw materials: 400 g of the Au—Pd/TS-1 catalyst obtained in step (1) was mixed with 9600 g of water to obtain a suspension liquid at a mass concentration of 4%; and 200 g of glycol sulfite was mixed with 800 g of dichloroethane to prepare a glycol sulfite-dichloroethane solution with a mass fraction of glycol sulfite of 20%, for later use.

(3) Continuous flow synthesis reaction: the suspension liquid obtained in step (2) was pumped into a premixing zone of a flow reactor, and at the same time, hydrogen and oxygen were introduced thereinto; a temperature of the premixing zone was controlled to be 30° C., a residence time of the suspension liquid in the premixing zone was controlled to be 40 s, and a premixed liquid was obtained; and a volume ratio of the hydrogen and the oxygen in the gas mixture was 1:1;

the premixed liquid entered a reaction zone after flowing out of the premixing zone, and at the same time, the glycol sulfite-dichloroethane solution obtained in step (2) was pumped into the reaction zone; a temperature of the reaction zone was controlled to be 60° C., a residence time of a reaction was controlled to be 100 s, and a reaction liquid was obtained, which flowed out of the reactor; the Au—Pd/TS-1 catalyst was separated by a filter, and an obtained filtrate was processed by a centrifugal separator to obtain an aqueous phase and an organic phase; a mass ratio of the glycol sulfite to the oxygen introduced into the premixing zone was 108:50; and a mass of the oxygen introduced into the premixing zone was 92.6 g; and the same volume of deionized water was added to the organic phase, followed by pumping into a centrifugal extractor for liquid separation to obtain an organic phase solution, and the obtained organic phase solution was distilled and crystallized to obtain a DTD product.

Example 4 A method for synthesizing DTD by in-situ catalytic oxidation includes the following steps.

(1) Preparation of Au—Pd/TS-1 catalyst: 5 g of Pd(OAc)$_2$, 5 g of PdCl$_2$, 8 g of AuCl$_3$ and 6 g of HAuCl$_4$·3H$_2$O were dissolved in 3 kg of water, and 950 g of TS-1 molecular sieve was added, followed by stirring uniformly, and reacting for 15 h at a temperature raised to be 70° C., and a reaction liquid was obtained, which was subjected to air-blast drying to remove water to obtain white powder, which was put into a tube furnace for reduction treatment at 420° C. for 2 h to obtain an Au—Pd/TS-1 catalyst. The tube furnace had an atmosphere of a gas mixture of hydrogen and argon, and the hydrogen in the gas mixture was at a volume concentration of 8%.

(2) Preparation of raw materials: 800 g of the Au—Pd/TS-1 catalyst obtained in step (1) was mixed with 9200 g of water to obtain a suspension liquid at a mass concentration of 8%; and 400 g of glycol sulfite was mixed with 600 g of dichloroethane to prepare a glycol sulfite-dichloroethane solution with a mass fraction of glycol sulfite of 40%, for later use.

(3) Continuous flow synthesis reaction: the suspension liquid obtained in step (2) was pumped into a premixing zone of a flow reactor, and hydrogen and oxygen were introduced thereinto; a temperature of the premixing zone was controlled to be 65° C., a residence time of the suspension liquid in the premixing zone was controlled to be 40 s, and a premixed liquid was obtained; and a volume ratio of the hydrogen to the oxygen was 1:1;

the premixed liquid entered a reaction zone after flowing out of the premixing zone, and at the same time, the glycol sulfite-dichloroethane solution obtained in step (2) was pumped into the reaction zone; a temperature of the reaction zone was controlled to be 50° C., a residence time of a reaction was controlled to be 400 s, and a reaction liquid was obtained, which flowed out of the reactor; the Au—Pd/TS-1 catalyst was separated by a filter, and an obtained filtrate was processed by a centrifugal separator to obtain an aqueous phase and an organic phase; a mass ratio of the glycol sulfite to the oxygen introduced into the premixing zone was 108:40; and a mass of the oxygen introduced into the premixing zone was 148.1 g; and the same volume of deionized water was added to the organic phase, followed by pumping into a centrifugal extractor for liquid separation to obtain an organic phase solution, and the obtained organic phase solution was distilled and crystallized to obtain a DTD product.

Example 5 A method for synthesizing DTD by in-situ catalytic oxidation includes the following steps.

(1) Preparation of Au—Pd/TS-1 catalyst: 10 g of Pd(OAc)$_2$ and 10 g of HAuCl$_4$·3H$_2$O were dissolved in 2 kg of water, and 980 g of TS-1 molecular sieve was added, followed by stirring uniformly, and reacting for 20 h at a temperature raised to be 90° C., and a reaction liquid was obtained, which was subjected to air-blast drying to remove water to obtain white powder, which was put into a tube furnace for reduction treatment at 400° C. for 2.5 h to obtain an Au—Pd/TS-1 catalyst. The tube furnace had an atmosphere of a gas mixture of hydrogen and argon, and the hydrogen in the gas mixture was at a volume concentration of 8%.

(2) Preparation of raw materials: 600 g of the Au—Pd/TS-1 catalyst obtained in step (1) was mixed with 9400 g of water to obtain a suspension liquid at a mass concentration of 6%; and 400 g of glycol sulfite was mixed with 600 g of dichloroethane to prepare a glycol sulfite-dichloroethane solution with a mass fraction of glycol sulfite of 40%, for later use.

(3) Continuous flow synthesis reaction: the suspension liquid obtained in step (2) was pumped into a premixing zone of a flow reactor, and at the same time, hydrogen and oxygen were introduced thereinto; a temperature of the premixing zone was controlled to be 60° C., a residence time of the suspension liquid in the premixing zone was controlled to be 50 s, and a premixed liquid was obtained; and a volume ratio of the hydrogen and the oxygen in the gas mixture was 1:1;

the premixed liquid entered a reaction zone after flowing out of the premixing zone, and at the same time, the glycol sulfite-dichloroethane solution obtained in step (2) was pumped into the reaction zone; a temperature of the reaction zone was controlled to be 55° C. a residence time of a reaction was controlled to be 450 s, and a reaction liquid was obtained, which flowed out of the reactor; the Au—Pd/TS-1 catalyst was separated by a filter, and an obtained filtrate was processed by a centrifugal separator to obtain an aqueous phase and an organic phase; a mass ratio of the glycol sulfite to the oxygen introduced into the premixing zone was 108:60; and a mass of the oxygen introduced into the premixing zone in step (3) was 222.2 g; and the same volume of deionized water was added to the organic phase, followed by pumping into a centrifugal extractor for liquid separation to obtain an organic phase solution, and the obtained organic phase solution was distilled and crystallized to obtain a DTD product.

The introduction of hydrogen and oxygen in Examples 1-5 is a continuous process, and it is ensured that hydrogen and oxygen can be introduced continuously in this process. The introduced amount of oxygen can be 1.2-1.5 times the expected amount, to allow for the full reaction of glycol sulfite.

FIG. 1 shows the SEM characterization of the Au—Pd/TS-1 (Au—Pd@TS-1) catalyst, from which it can be seen that TS-1 as the main structure of the catalyst is loaded with Au and Pd nanoparticles, i.e., the Au—Pd@TS-1 modified catalyst is successfully synthesized.

Figure 2:
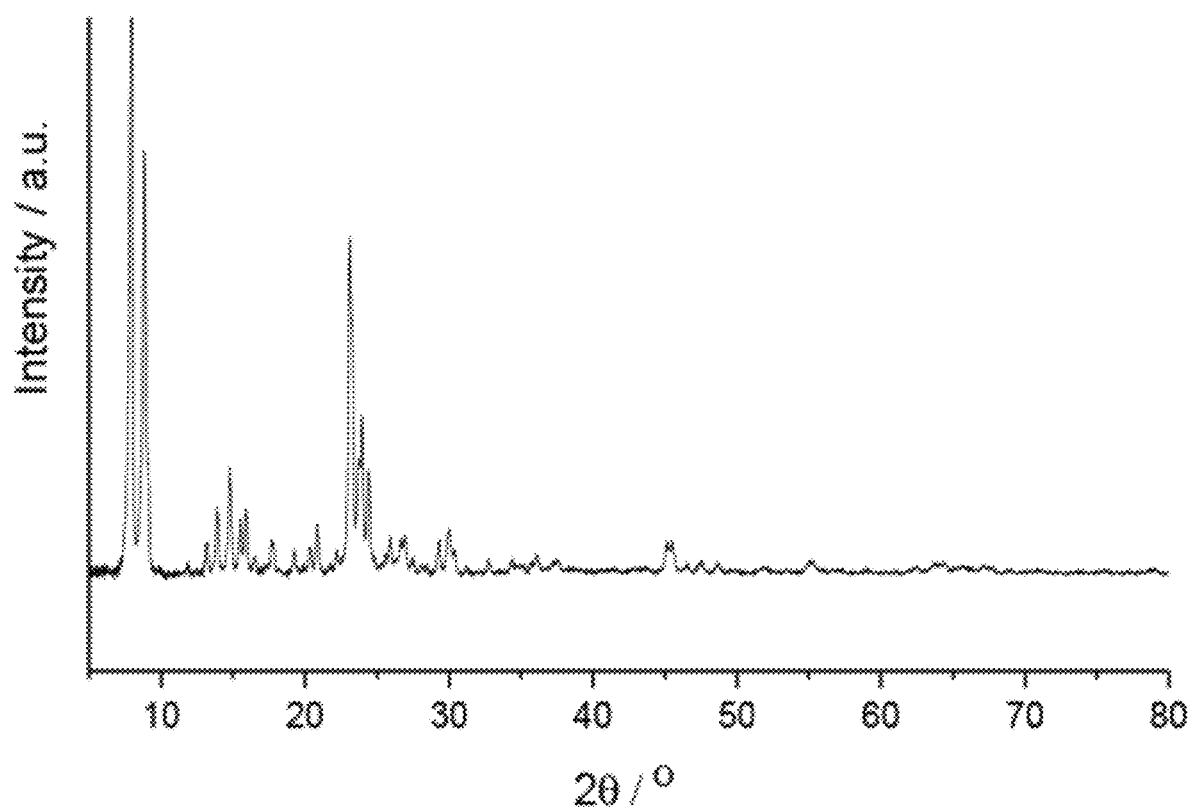
FIG. 2 shows the X-ray diffraction (XRD) characterization of the Au—Pd/TS-1 catalyst.

FIG. 2 shows the XRD characterization of the Au—Pd/TS-1 catalyst, from which it can be seen that the modified catalyst basically retains the TS-1 crystal structure, and has characteristic peaks basically consistent with those of the standard TS-1 molecular sieve, indicating that the modified catalyst still possesses the excellent crystalline properties of TS-1 molecular sieve.

Figure 4:
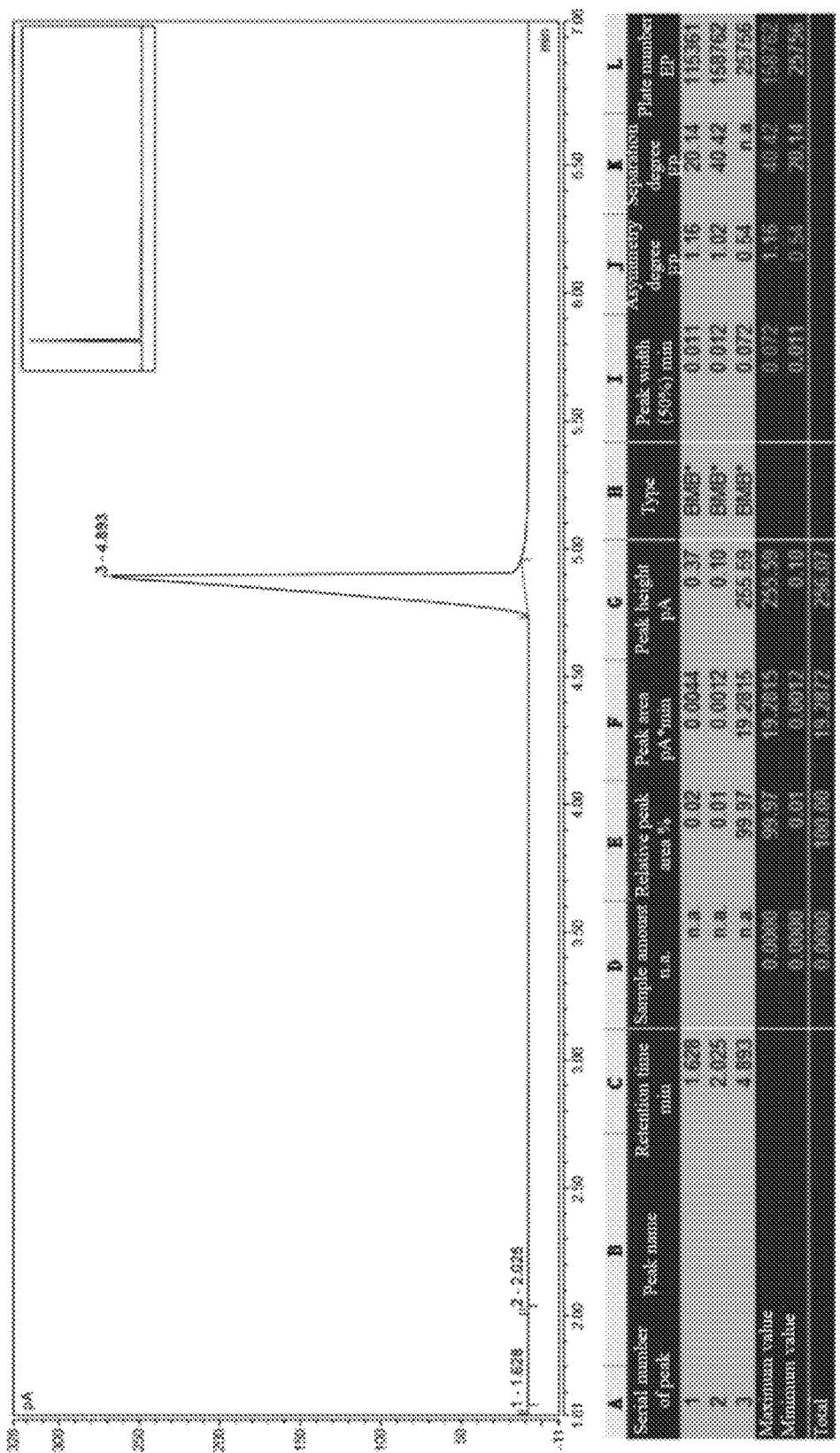
FIG. 4 shows a gas chromatogram of a DTD product obtained in Example 5.

According to the method of synthesizing DTD by in-situ catalytic oxidation in Examples 1-5, the developed Au—Pd/TS-1 catalyst is employed to synthesize hydrogen peroxide to directly oxidize glycol sulfite, and the high-efficiency output of DTD products can be realized by means of the continuous flow reaction technology. Generally, the yield of DTD can reach 95% or more by the amount of glycol sulfite. The Au—Pd/TS-1 catalyst can be used repeatedly, and the product DTD is at a purity of 99.9% or more, and as shown in FIG. 4, DTD obtained in Example 5 is at a purity of 99.97%.

The invention claimed is:

1. A method for synthesizing 1,3,2-dioxathiolane 2,2-dioxide (DTD) by in-situ catalytic oxidation, comprising the following steps:
   (1) preparation of Au—Pd/titanium silicon (TS)-1 catalyst: dissolving a Pd salt and an Au salt in water, adding a TS-1 molecular sieve, followed by stirring uniformly, reacting for 8-24 h at a temperature raised to be 60-105°

C., to obtain a reaction liquid, performing air-blast drying on the reaction liquid to remove the water to obtain white powder, and putting the obtained white powder into a tube furnace for reduction treatment at 350-450° C. for 2-3 h to obtain an Au—Pd/TS-1 catalyst, wherein the tube furnace has an atmosphere of a gas mixture of hydrogen and argon, the hydrogen in the gas mixture being at a volume concentration of 5-10%;

the Pd salt is one or two of $PdCl_2$, $PdSO_4$, $Pd(NO_3)_2 \cdot 2H_2O$ or $Pd(OAc)_2$;

the Au salt is $AuCl_3$ and/or $HAuCl_4 \cdot 3H_2O$; and a mass ratio of the Pd salt, the Au salt, the TS-1 molecular sieve and the water is 8-12 g:8-15 g:0.9-1 kg:1-5 kg;

(2) preparation of raw materials: mixing the Au—Pd/TS-1 catalyst obtained in step (1) with water to obtain a suspension liquid at a mass concentration of 1-10%; and mixing glycol sulfite with dichloroethane to prepare a glycol sulfite-dichloroethane solution with a mass fraction of glycol sulfite of 10-60%, for later use; and (3) continuous flow synthesis reaction: pumping the suspension liquid obtained in step (2) into a premixing zone of a flow reactor, introducing hydrogen and oxygen thereinto at the same time, and controlling a temperature of the premixing zone to be 10-90° C. and a residence time of the suspension liquid in the premixing zone to be 3-60 s, to obtain a premixed liquid, a volume ratio of the hydrogen to the oxygen being 1:1;

the premixed liquid entering a reaction zone after flowing out of the premixing zone, pumping the glycol sulfite-dichloroethane solution obtained in step (2) into the reaction zone at the same time, controlling a temperature of the reaction zone to be 10-90° C. and a residence time of a reaction to be 15-600 s, to obtain a reaction liquid, which flows out of the reactor, separating the Au—Pd/TS-1 catalyst by a filter, and processing an obtained filtrate by a centrifugal separator to obtain an aqueous phase and an organic phase; and adding the same volume of deionized water to the organic phase, followed by pumping into a centrifugal extractor for liquid separation to obtain an organic phase solution, and distilling and crystallizing the obtained organic phase solution to obtain a DTD product.

2. The method for synthesizing DTD by in-situ catalytic oxidation according to claim 1, wherein the Pd salt is $PdCl_2$ or $Pd(OAc)_2$; and the Au salt is $HAuCl_4 \cdot 3H_2O$.

3. The method for synthesizing DTD by in-situ catalytic oxidation according to claim 1, wherein a mass of the water added in step (1) is twice a total mass of the TS-1 molecular sieve and the two metal salts, and the mass ratio of the Pd salt, the Au salt, the TS-1 molecular sieve and the water is 10 g:10 g:980 g:2 kg.

4. The method for synthesizing DTD by in-situ catalytic oxidation according to claim 1, wherein in step (3), a mass ratio of the suspension liquid obtained in step (2) to the gas mixture is 1:1-2.

5. The method for synthesizing DTD by in-situ catalytic oxidation according to claim 1, wherein in step (3), a mass ratio of the glycol sulfite to the oxygen introduced to the premixing zone is 108:32-64.

6. The method for synthesizing DTD by in-situ catalytic oxidation according to claim 1, wherein a temperature of the premixing zone is 60-65° C., and a temperature of the reaction zone is 50-55° C.

7. The method for synthesizing DTD by in-situ catalytic oxidation according to claim 1, wherein the residence time of the suspension liquid in the premixing zone is 40-50 s, and the residence time of the reaction is 400-450 s.

* * * * *